(12) United States Patent
Maier

(10) Patent No.: US 8,583,209 B2
(45) Date of Patent: Nov. 12, 2013

(54) METHOD AND SYSTEM FOR MONITORING CARDIAC FUNCTION OF A PATIENT DURING A MAGNETIC RESONANCE IMAGING (MRI) PROCEDURE

(75) Inventor: Corinna Maier, Princeton, NJ (US)

(73) Assignee: Siemens Aktiengesellschaft, München (DE)

( * ) Notice: Subject to any disclaimer, the term of this patent is extended or adjusted under 35 U.S.C. 154(b) by 573 days.

(21) Appl. No.: 12/237,467

(22) Filed: Sep. 25, 2008

(65) Prior Publication Data

US 2009/0093707 A1   Apr. 9, 2009

Related U.S. Application Data

(60) Provisional application No. 60/977,211, filed on Oct. 3, 2007.

(51) Int. Cl.
*A61B 5/055* (2006.01)

(52) U.S. Cl.
USPC ............ 600/410; 382/128; 382/131; 382/132

(58) Field of Classification Search
None
See application file for complete search history.

(56) References Cited

U.S. PATENT DOCUMENTS

| | | | |
|---|---|---|---|
| 4,945,478 A * | 7/1990 | Merickel et al. | 382/131 |
| 5,161,204 A * | 11/1992 | Hutcheson et al. | 382/157 |
| 6,044,171 A | 3/2000 | Polyakov et al. | |
| 6,885,772 B2 | 4/2005 | DeLong | |
| 6,961,454 B2 | 11/2005 | Jolly | |
| 7,095,890 B2 | 8/2006 | Paragios et al. | |
| 2003/0069494 A1 * | 4/2003 | Jolly | 600/410 |
| 2004/0024306 A1 * | 2/2004 | Hamilton et al. | 600/410 |
| 2005/0059876 A1 * | 3/2005 | Krishnan et al. | 600/407 |
| 2005/0192502 A1 * | 9/2005 | Ishiyama et al. | 600/508 |
| 2007/0041639 A1 * | 2/2007 | Von Berg et al. | 382/173 |
| 2007/0135705 A1 | 6/2007 | Lorenz et al. | |
| 2008/0260230 A1 * | 10/2008 | Gotardo et al. | 382/131 |

OTHER PUBLICATIONS

Lin et al. "classification of partial 2-D shapes using Fourier descriptors", (I.E.E.E. Transactions on Pattern Analysis and Machine Intelligence, vol. PAMI-9 No. 5, pp. 686-690, 1987).*

* cited by examiner

*Primary Examiner* — Long V. Le
*Assistant Examiner* — Farshad Negarestan
(74) *Attorney, Agent, or Firm* — Donald B. Paschburg; F. Chau & Associates, LLC

(57) ABSTRACT

A method for monitoring cardiac function of a patient during a magnetic resonance imaging (MRI) procedure, including: acquiring an MR image sequence of the patient's heart during a cardiac phase; segmenting a left ventricle of the patient's heart in the MR image sequence, wherein the segmentation produces endocardial and epicardial contours; representing at least one of the contours in polar or radial coordinates and computing its Fourier transform, wherein the Fourier transform produces Fourier descriptors for the contour; putting a vector of the Fourier descriptors into a classifier, wherein the classifier determines whether the contour reflects normal wall motion in the cardiac phase or whether the contour reflects abnormal wall motion in the cardiac phase; and alerting a medical practitioner when abnormal wall motion is detected.

26 Claims, 8 Drawing Sheets

METHOD AND SYSTEM FOR MONITORING CARDIAC FUNCTION OF A PATIENT DURING A MAGNETIC RESONANCE IMAGING (MRI) PROCEDURE

CROSS-REFERENCE TO RELATED APPLICATION

This application claims the benefit of U.S. Provisional Application No. 60/977,211, filed Oct. 3, 2007, the disclosure of which is incorporated by reference herein in its entirety.

BACKGROUND OF THE INVENTION

1. Technical Field

The present invention relates to monitoring cardiac function of a patient during a magnetic resonance imaging (MRI) procedure, and more particularly, a method and system for monitoring cardiac function of a patient during an MRI procedure without an electrocardiogram (ECG).

2. Discussion of the Related Art

Catheterization based methods like angioplasty, valve replacement, stent replacement, and ablation for atrial fibrillation are widely performed under X-ray monitoring and guidance. These methods, however, involve the use of ionizing radiation, which is a risk for the patient and the medical personnel conducting the procedure. Magnetic resonance imaging (MRI) would be a preferable alternative to X-ray, not only because of its lack of ionizing radiation, but also because it provides superior soft tissue contrast in images. One of the major challenges of interventional MRI is patient safety during the procedure. For example, standard monitoring devices, such as an electrocardiogram (ECG), are disturbed by the magnetic field environment and cannot be interpreted during MRI. See e.g., [Fischer, S. E., et al. (1999), "Novel real-time R-wave detection algorithm based on the vectorcardiogram for accurate gated magnetic resonance acquisitions", Magn Reson Med. Vol. 42(2), pp. 361-370]. Yet, real-time updates on heart function and structure during an MRI procedure are critical for interventional cardiovascular MRI, in particular, as well as for diagnostic dobutamine stress testing with MRI.

Accordingly, there is a need for a technique that enables real-time updates on heart function during an MRI procedure.

SUMMARY OF THE INVENTION

In an exemplary embodiment of the present invention, a method for monitoring cardiac function of a patient during a magnetic resonance imaging (MRI) procedure, comprises: acquiring an MR image sequence of the patient's heart during a cardiac phase; segmenting a left ventricle of the patient's heart in the MR image sequence, wherein the segmentation produces endocardial and epicardial contours; representing at least one of the contours in polar or radial coordinates and computing its Fourier transform, wherein the Fourier transform produces Fourier descriptors for the contour; putting a vector of the Fourier descriptors into a classifier, wherein the classifier determines whether the contour reflects normal wall motion in the cardiac phase or whether the contour reflects abnormal wall motion in the phase; and alerting a medical practitioner when abnormal wall motion is detected.

The classifier is trained.

The classifier is trained prior to start of the MRI procedure by observing normal wall motion during systole and diastole cardiac phases of the patient's heart and setting a baseline threshold for the normal wall motion in each of these phases.

The training is supervised or unsupervised.

The classifier computes a confidence measure that is compared against the baseline threshold for the normal wall motion in the systole and diastole cardiac phases and if the confidence measure is below its respective baseline threshold the contour reflects abnormal wall motion.

The method further comprises displaying real-time images of the patient's heart during the MRI procedure.

The wall is a myocardial wall.

The MRI procedure comprises an MRI-guided intervention or an MRI stress test.

When the classifier determines that the contour reflects normal wall motion the contour is classified as systole or diastole, the method further comprises: acquiring a next MR image sequence of the patient's heart during a next cardiac phase; segmenting the left ventricle of the patient's heart in the next MR image sequence, wherein the segmentation produces next endocardial and epicardial contours; representing at least one of the next contours in polar or radial coordinates and computing its Fourier transform, wherein the Fourier transform produces Fourier descriptors for the next contour; putting a vector of the Fourier descriptors for the next contour into the classifier, wherein the classifier classifies the next contour as systole or diastole; analyzing the contour classifications made by the classifier during the original and next cardiac phases; and alerting the medical practitioner that abnormal wall motion has been detected when the contour classification is the same in both the original and next cardiac phases.

In an exemplary embodiment of the present invention, a system for monitoring cardiac function of a patient during an MRI procedure, comprises: a memory device for storing a program: a processor in communication with the memory device, the processor operative with the program to: acquire an MR image sequence of the patient's heart during a cardiac phase; segment a left ventricle of the patient's heart in the MR image sequence, wherein the segmentation produces endocardial and epicardial contours; represent at least one of the contours in polar or radial coordinates and compute its Fourier transform, wherein the Fourier transform produces Fourier descriptors for the contour; put a vector of the Fourier descriptors into a classifier, wherein the classifier determines whether the contour reflects normal wall motion in the cardiac phase or whether the contour reflects abnormal wall motion in the cardiac phase; and alert a medical practitioner when abnormal wall motion is detected.

The classifier is trained.

The classifier is trained prior to start of the MRI procedure by observing normal wall motion during systole and diastole cardiac phases of the patient's heart and setting a baseline threshold for the normal wall motion in each of these phases.

The training is supervised or unsupervised.

The classifier computes a confidence measure that is compared against the baseline threshold for the normal wall motion in the systole and diastole cardiac phases and if the confidence measure is below its respective baseline threshold the contour reflects abnormal wall motion.

The processor is further operative with the program to display real-time images of the patient's heart during the MRI procedure.

The wall is a myocardial wall.

The MRI procedure comprises an MRI-guided intervention or an MRI stress test.

In an exemplary embodiment of the present invention, a computer readable medium tangibly embodying a program of instructions executable by a processor to perform method steps for monitoring cardiac function of a patient during an MRI procedure is provided, the method steps comprising:

acquiring an MR image sequence of the patient's heart during a cardiac phase; segmenting a left ventricle of the patient's heart in the MR image sequence, wherein the segmentation produces endocardial and epicardial contours; representing at least one of the contours in polar or radial coordinates and computing its Fourier transform, wherein the Fourier transform produces Fourier descriptors for the contour; putting a vector of the Fourier descriptors into a classifier, wherein the classifier determines whether the contour reflects normal wall motion in the cardiac phase or whether the contour reflects abnormal wall motion in the cardiac phase; and alerting a medical practitioner when abnormal wall motion is detected.

The classifier is trained.

The classifier is trained prior to start of the MRI procedure by observing normal wall motion during systole and diastole cardiac phases of the patient's heart and setting a baseline threshold for the normal wall motion in each of these phases.

The training is supervised or unsupervised.

The classifier computes a confidence measure that is compared against the baseline threshold for the normal wall motion in the systole and diastole cardiac phases and if the confidence measure is below its respective baseline threshold the contour reflects abnormal wall motion.

The method steps further comprise displaying real-time images of the patient's heart during the MRI procedure.

The wall is a myocardial wall.

The MRI procedure comprises an MRI-guided intervention or an MRI stress test.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Presented herein, in accordance with an exemplary embodiment of the present invention, is a novel image-based monitoring method for left ventricular (LV) myocardial wall motion. The aim of this method is to detect pathological wall motion changes by means of a shape classifier. In this method, the shape of the myocardial wall is represented by Fourier descriptors as a basis for both an accurate description and as input for a classification method. The term pathological is used in this disclosure to primarily describe hypokinesis or akinesis of the ischemic myocardial wall. We assume that enough patient individual non-pathological images have been acquired to train the classifier before a pathological event occurs.

Figure 1:
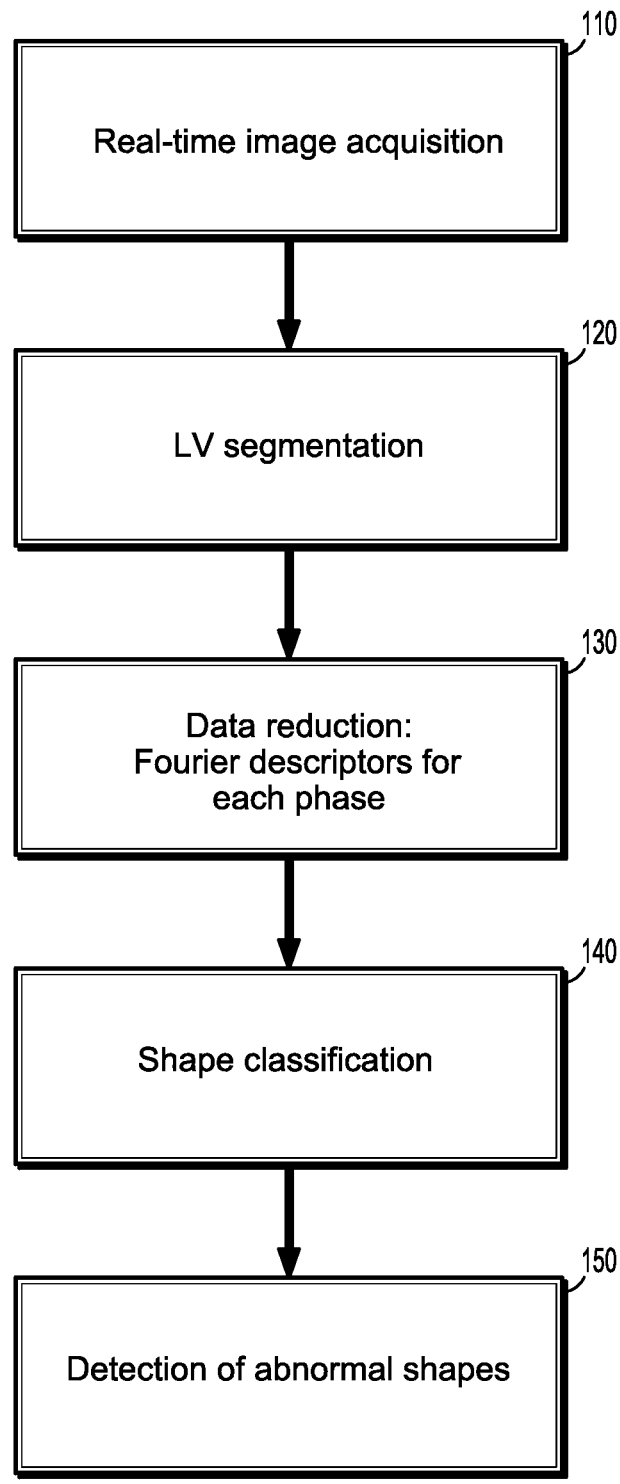
FIG. 1 is a flow diagram of a method in accordance with an exemplary embodiment of the present invention.

FIG. 1 illustrates the main stages of our method.

In our method, the approach we take is to establish a baseline level of wall motion based on patient-specific images acquired in a baseline portion of an examination. In other words, prior to starting an MRI procedure, which may be interventional cardiovascular MRI or diagnostic dobutamine stress testing with MRI, for example, we train a classifier to set a baseline threshold for normal wall motion in systole and diastole cardiac phases.

In the MRI procedure real-time images of the patient's heart are acquired during a cardiac phase (110) and the left ventricle of the patient's heart is segmented (120). At least one of the contours (e.g., endocardial or epicardial) is represented in polar or radial coordinates and its Fourier transform is calculated to produce Fourier descriptors therefor (130). A vector of the Fourier descriptors is input to a classifier and the classifier determines whether the contour corresponds to the previously determined normal wall motion for its respective cardiac phase or whether the contour reflects abnormal wall motion (140). If the contour reflects abnormal wall motion, due to ischemia, for example, a medical practitioner performing the MRI procedure is prompted to pause the procedure and view real-time images of the patient's heart on a display (150). The prompt may be an alarm sounding, for example.

Some aspects of the method shown in FIG. 1 are now discussed in detail.

The segmentation can be performed by an offline segmentation method, such as the one described in [Jolly, M. (2006), "Automatic Segmentation of the Left Ventricle in Cardiac MR and CT images", Vol. 70, Kluwer Academic Publishers, Hingham, Mass., USA], which has been modified to estimate the endocardial (inner) and epicardial (outer) contours of the LV myocardial wall.

Figure 2A:
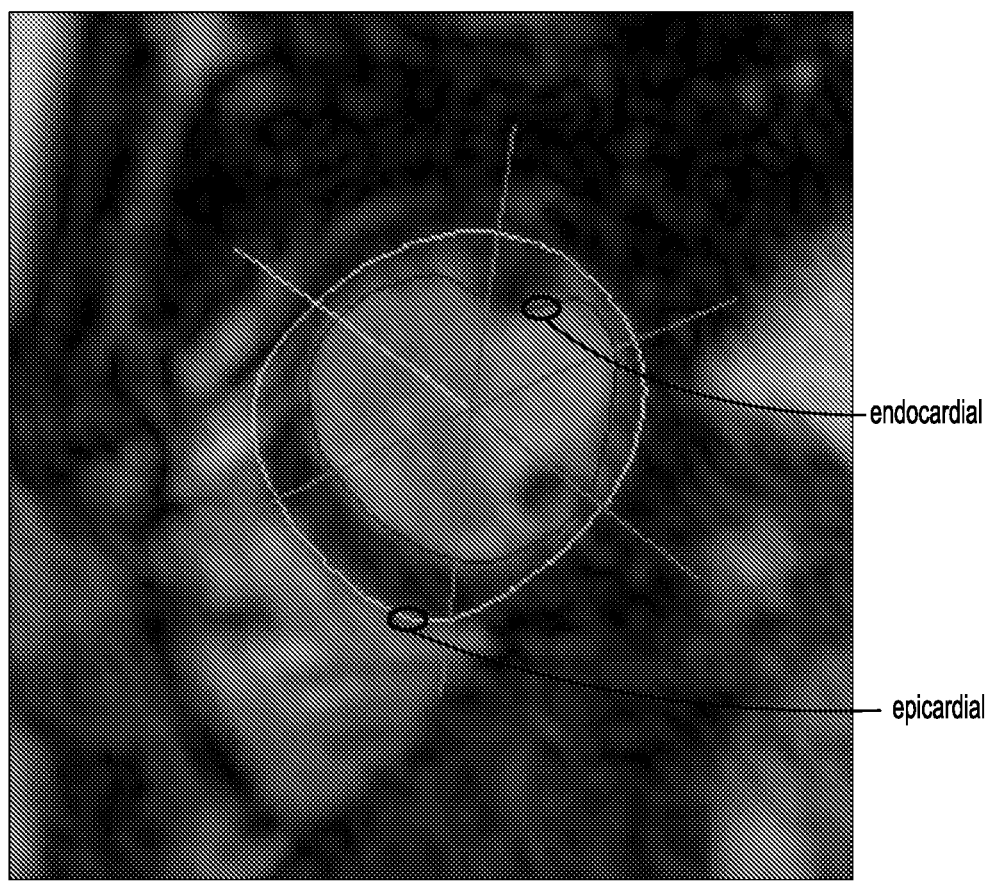
FIG. 2A shows endocardial and epicardial contours in a mid-ventricular phase image, after segmentation in accordance with an exemplary embodiment of the present invention.

The propagation method described by Jolly relies on the availability of all phases for an entire cardiac cycle. In a real-time image scenario, however, we do not have any phase information about the current cycle. We therefore changed Jolly's algorithm such that the propagation copies the contours from a predecessor image to a next one before local deformation is applied. FIG. 2(A) shows an example of a mid-ventricular MR image with its LV contours.

Any segmentation method giving the inner contour in two-dimension (2D) or three-dimension (3D) could be used in our method, for example.

The contours/boundaries are represented in polar coordinates with respect to the center of gravity of the endocardial contours $(x_c, y_c)$, for example. The contour is sampled as distance $r(\alpha)$ of the boundary points $(x(\alpha), y(\alpha))$ from the center:

$$r(\alpha) = ([x(\alpha) - x_c]^2 + [y(\alpha) - y_c]^2)^{1/2}.$$

Figure 2B:
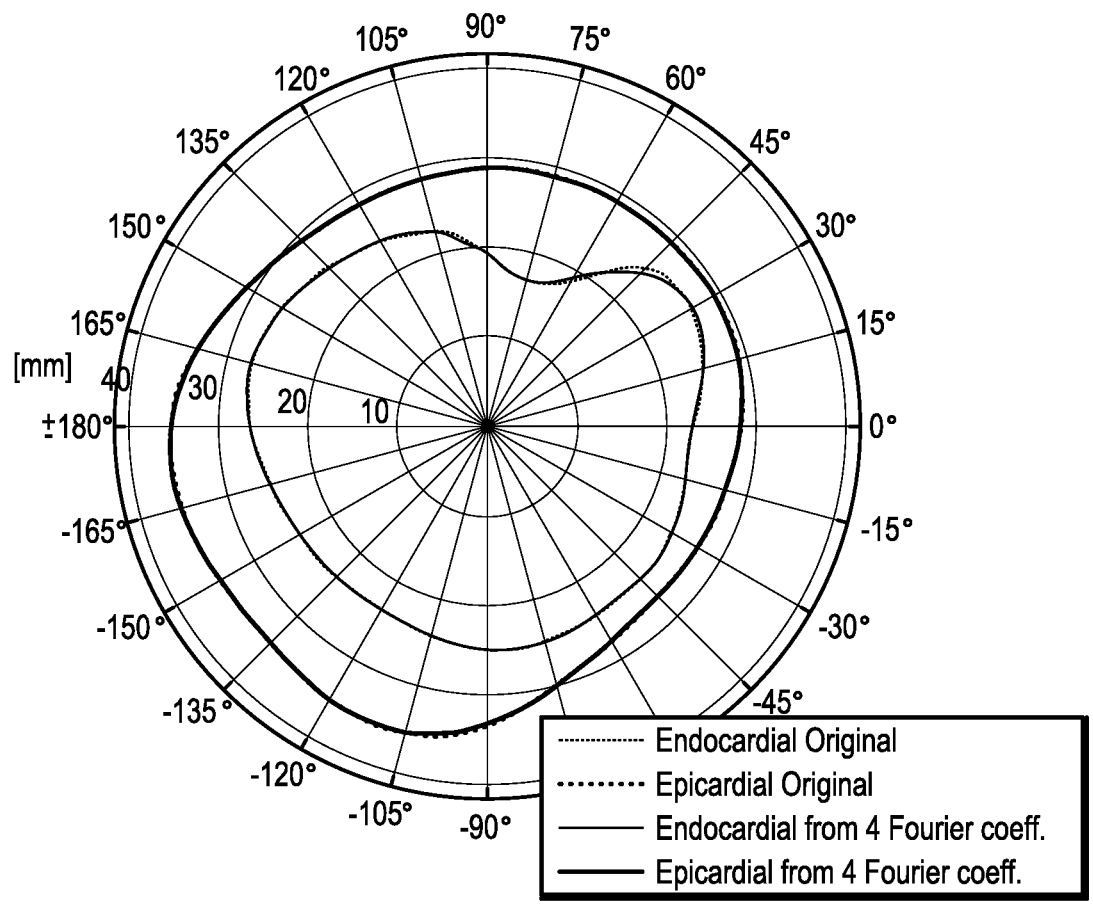
FIG. 2B shows the contours of FIG. 2A in a polar plot, in accordance with an exemplary embodiment of the present invention.

Note that r(α) is invariant for translations. This is important since cardiac images might be translated due to breathing. For maximum computational efficiency the number of sampling points P for α should be chosen as a power of 2 since the contour will be used further as input of a Fast Fourier Transformation. FIG. 2(B) shows the centroid distance expressed for an endocardial contour and an epicardial contour.

With regard to the Fourier descriptors, see [Kuhl, F. P. and Giardina, C. R. (1982), "Elliptic Fourier features of a closed contour", Computer Graphics and Image Processing, Vol. 18, pp. 259-278] for a description thereof, we note that they have been successfully used in the past to model a 2D shape boundary of static or moving objects. See [Mowbray, S. and Nixon, M. (2004), "Extraction and recognition of periodically deforming objects by continuous, spatio-temporal shape description", 2004 IEEE Computer Science Conference on Computer Vision and Pattern Recognition (CVPR'04), Vol. 2, pp. 895-9011, for example.

We applied this concept to the contours, i.e., the shape boundary, of the LV wall. In our method, the number of Fourier descriptors is reduced and used as a feature for the classifier.

To calculate the Fourier descriptors we note that the cardiac contours form a closed curve. This curve can be considered to be periodic. Due to this periodicity, the shape's boundaries can be represented as a Fourier series which gives the Fourier coefficients $\alpha_n$, n=0 . . . P−1. To achieve rotation invariance, the phase of the Fourier coefficients is ignored and only the magnitude $|\alpha_n|$ is used as a Fourier descriptor:

$$FD_n = |\alpha_n|, n=0, \ldots P-1.$$

This method for calculating Fourier descriptors could also be applied to 3D surfaces instead of 2D contours, for example.

The classifier could be one that, just considers the current state of the observation vector, or a classifier that is like a Hidden Markov Model, which considers previous and current states of the observation vector. The first class contains LV contours where the myocardial wall is relaxed (end-diastole) and no contraction is visible. The second class contains LV contours of a contracted myocardial wall (during systole). See FIG. 3B for an example of the first and second classes. The above-computed Fourier descriptors are used as observation vectors. Since we are only interested in shape but not scale, we exclude the first Fourier descriptor $FD_0$ from the feature vector that reflects the mean radius of the contour.

To detect shapes that do not belong to either class, we introduce a confidence measure: i.e., the logarithms of the unconditional, predictive probability of the observation x:

$$p(x) = \sum_C p(x \mid c_j) \cdot p(c_j) \geq \varepsilon$$

where $c_j$ is $c_1$ for class 1 (no contraction) and $c_2$ for class 2 (contraction), respectively, and $\varepsilon$ is the minimal unconditional predictive probability of the observation x to classify x in either of the classes.

For unsupervised learning, an agglomerative, hierarchical, clustering algorithm, see [Duda, R. O., et al. (2001), "Pattern Classification", Wiley], for example, can be used with a standardized Euclidean distance measure to reflect the different variances along different Fourier descriptors (the observation elements).

In detecting changes, two different kinds of changes might be observed. The changes could be: 1) changes on a certain location of the myocardial wall; or 2) that the wall is not contracting anymore. The first change is captured by the classification confidence measure. The second change results from the analysis of subsequent shapes. If no changes in shape are detected no contraction in the myocardium is assumed.

Figure 3A:
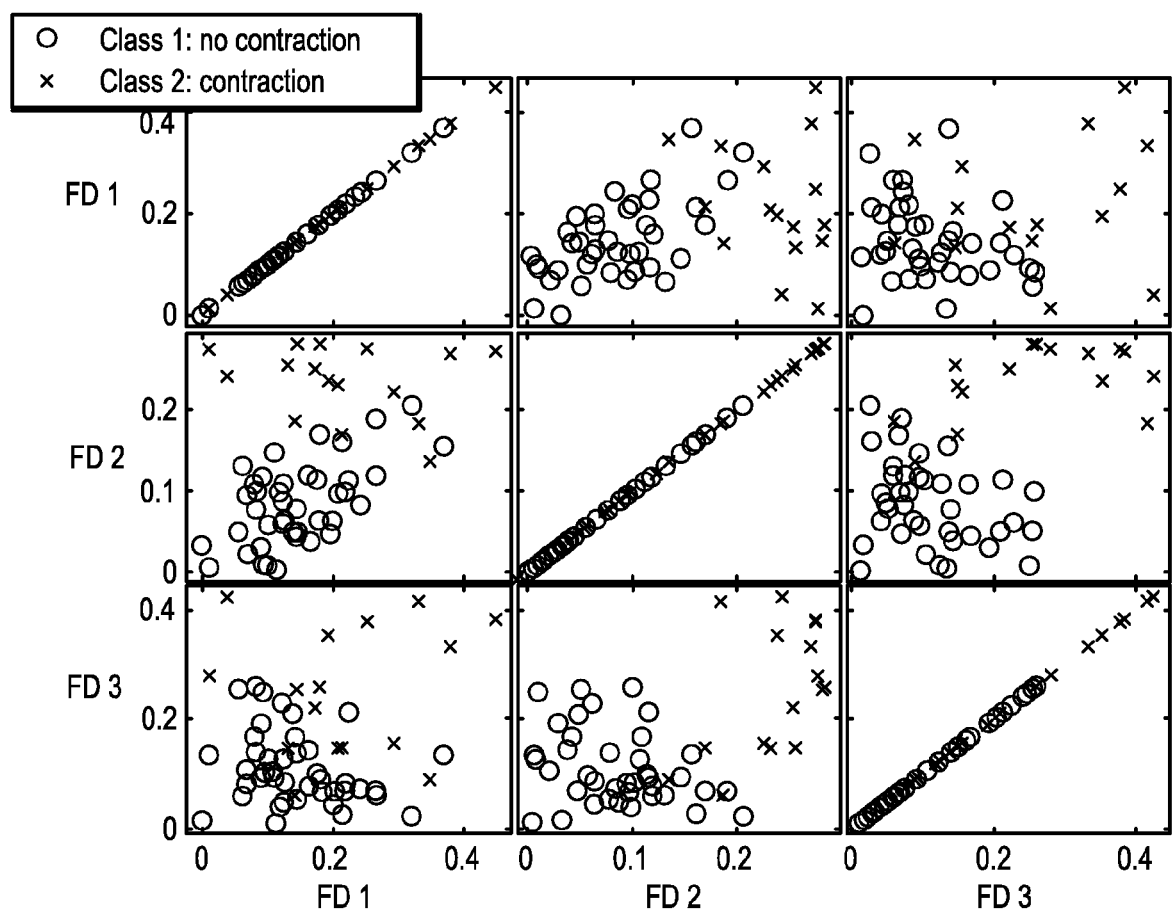
FIG. 3A shows separation between classes (no contraction/contraction) after supervised learning depending on classification factors, in accordance with an exemplary embodiment of the present invention.
Figure 3B:
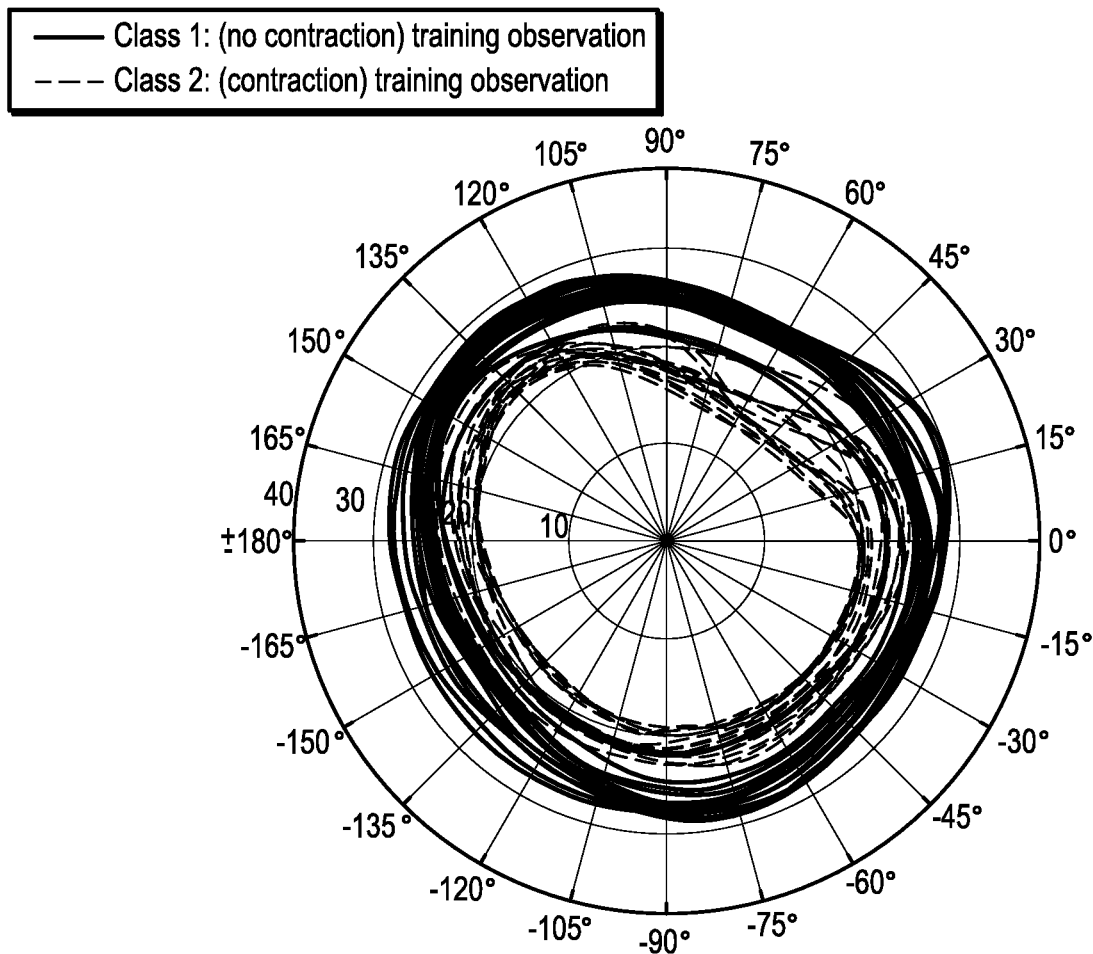
FIG. 3B shows labeled training observation contours for the classes (no contraction/contraction), in accordance with an exemplary embodiment of the present invention.
Figure 3C:
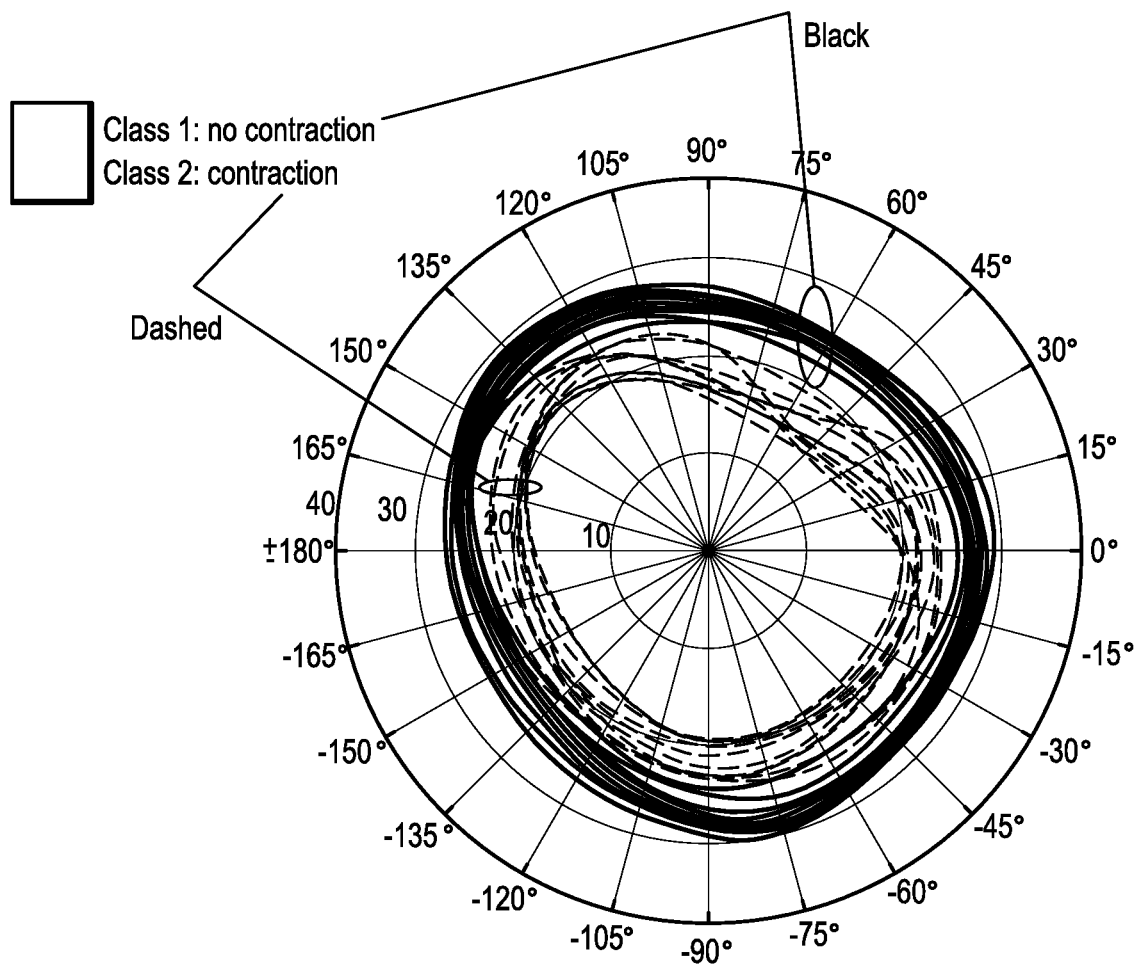
FIG. 3C shows classified sample contours for the classes (no contraction/contraction) with training data from FIG. 3B, in accordance with an exemplary embodiment of the present invention.
Figure 3D:
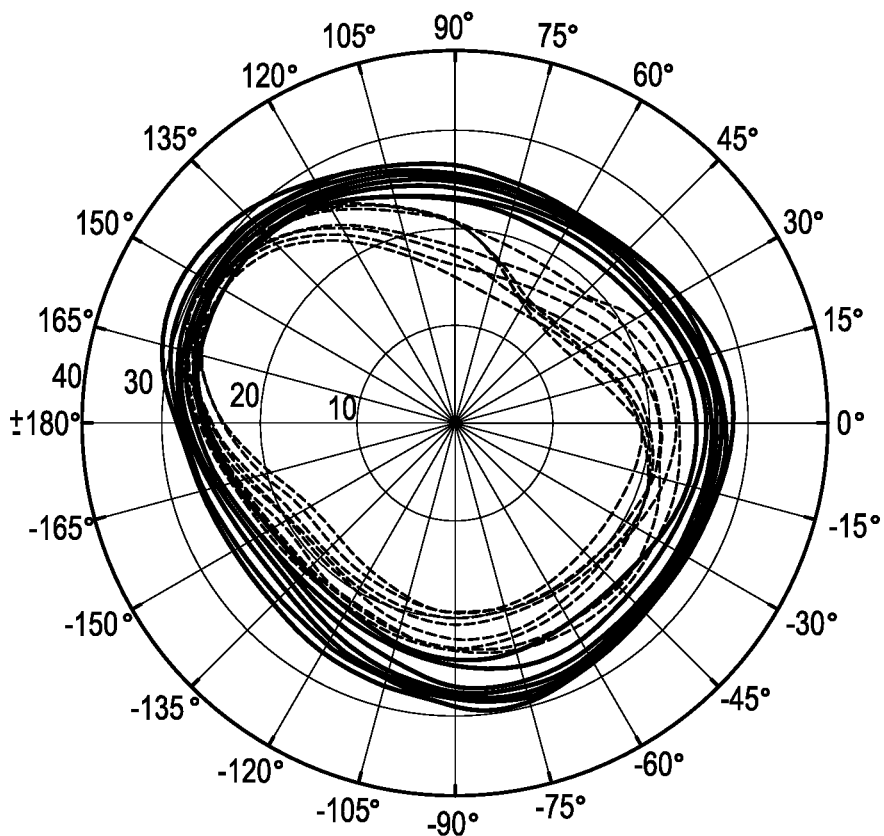
FIG. 3D shows classified (no contraction) and rejected abnormal contours (not classified), in accordance with an exemplary embodiment of the present invention.

FIGS. 3A-D show an example of a classifier instance. All data in these figures is from one patient at mid-ventricular position. The separation of this classifier is shown in FIG. 3A. FIG. 3B shows the first third of the contour data. This was manually labeled and used for supervised training of the classifier. FIG. 3C shows the remaining contour data (the other two thirds) which was then assigned to the first and second classes by the trained classifier. FIG. 3D shows the rejected contours. The input here was the remaining contours simulated by a model for ischemia. The model assumes that the myocardial wall does not contract where the ischemia is present.

The above-discussed framework for an online change detection of ischemic myocardial wall provides a method to monitor the cardiac physiological function of a patient during an MRI-guided intervention without the use of electrocardiogram (ECG). The method detects and reports the presence of an acute cardiac ischemic condition in a patient. The method evaluates the acquired image data by analyzing global features derived from the cardiac contour data. Global features include Fourier descriptors calculated from segmented inner (endocardial) and outer (epicardial) contours. A classifier evaluates the Fourier descriptors to determine whether an acute cardiac ischemic condition is detected. The classifier assigns a contour at one cardiac phase either to class contracted (systole) or non-contracted (diastole). A contour rejected by the classifier using the unconditional, predictive probability of the contour's observation vector as a confidence measure is interpreted as a pathological change in the LV myocardial wall motion. Hence, occurrence of myocardial ischemia can be detected by monitoring change in the myocardial contour's shapes.

Figure 4:
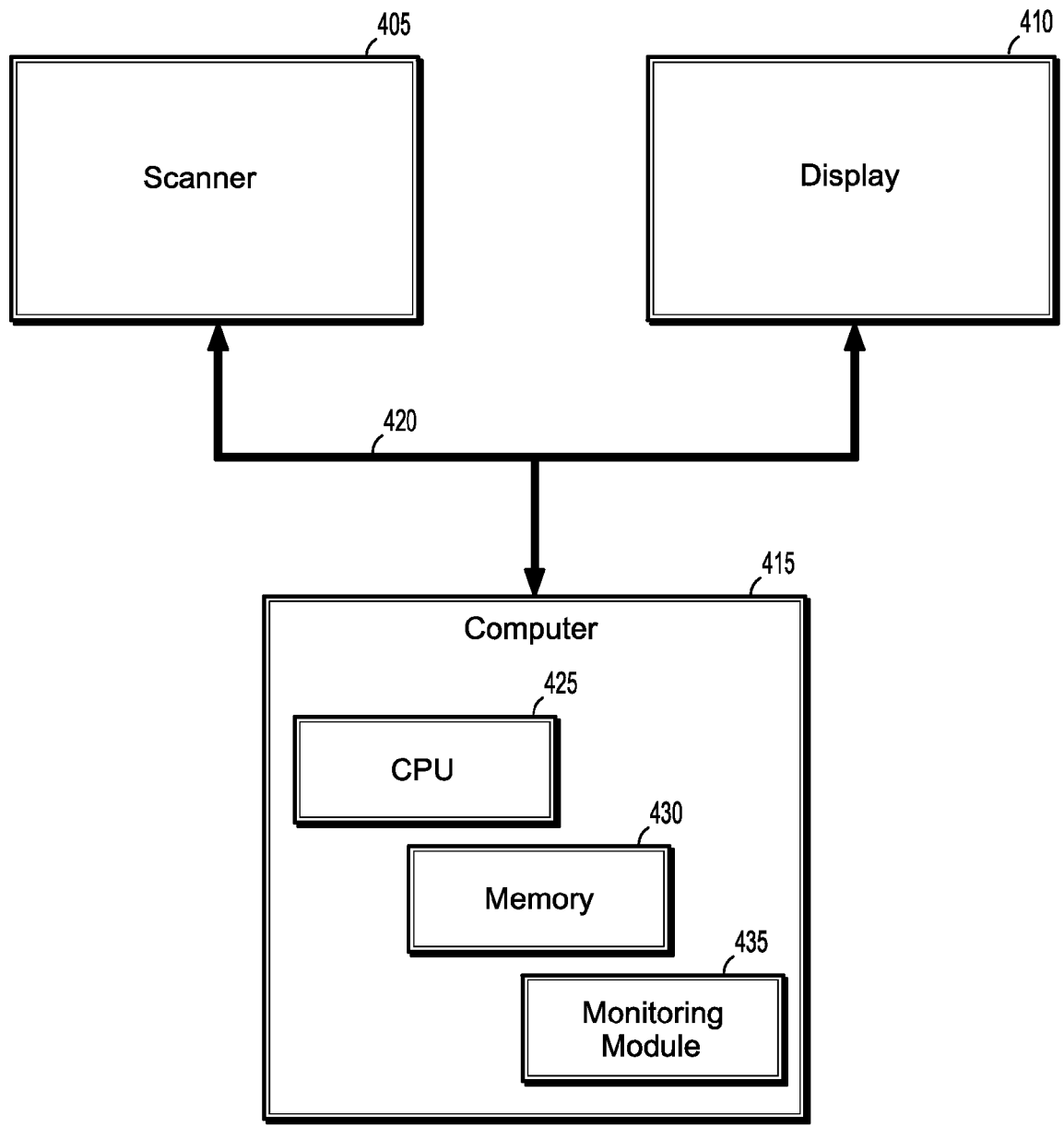
FIG. 4 is a block diagram of a system in which exemplary embodiments of the present invention may be implemented.

A system in which exemplary embodiments of the present invention may be implemented will now be described with reference to FIG. 4. As shown in FIG. 4, the system includes a scanner 405, a computer 415 and a display 410 connected over a wired or wireless network 420. The scanner 405 may be an MR or computed tomography (CT) scanner, for example. The computer 415 includes, inter alia, a central processing unit (CPU) 425, a memory 430 and a monitoring module 430 that includes program code for executing methods in accordance with exemplary embodiments of the present invention. The display 410 is a computer screen or television, for example.

It is understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is also understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It is further understood that the above description is only representative of illustrative embodiments. For convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for monitoring cardiac function of a patient during a magnetic resonance imaging (MRI) procedure, comprising:
    acquiring an MR image sequence of the patient's heart during a cardiac phase;
    segmenting a left ventricle of the patient's heart in the MR image sequence, wherein the segmentation produces endocardial and epicardial contours;
    representing at least one of the contours in polar or radial coordinates and computing its Fourier transform, wherein the Fourier transform produces Fourier descriptors for the contour;
    putting a vector of the Fourier descriptors into a classifier, wherein the classifier determines whether the contour reflects normal wall motion in the cardiac phase or whether the contour reflects abnormal wall motion in the cardiac phase, wherein a contour rejected by the classifier using an unconditional, predictive probability of the contour's observation vector as a confidence measure is interpreted as a pathological change in the left ventricle's myocardial wall motion, wherein contours reflective of abnormal wall motion are surrounded by contours reflective of normal wall motion in polar coordinates; and
    alerting a medical practitioner when abnormal wall motion is detected.

2. The method of claim 1, wherein the classifier is trained.

3. The method of claim 2, wherein the classifier is trained prior to start of the MRI procedure by observing normal wall motion during systole and diastole cardiac phases of the patient's heart and setting a baseline threshold for the normal wall motion in each of these phases.

4. The method of claim 3, wherein the training is supervised or unsupervised.

5. The method of claim 3, wherein the confidence measure is compared against the baseline threshold for the normal wall motion in the systole and diastole cardiac phases and if the confidence measure is below its respective baseline threshold the contour reflects abnormal wall motion.

6. The method of claim 1, further comprising:
    displaying real-time images of the patient's heart during the MRI procedure.

7. The method of claim 1, wherein the wall is a myocardial wall.

8. The method of claim 1, wherein the MRI procedure comprises an MRI-guided intervention or an MRI stress test.

9. The method of claim 1, wherein when the classifier determines that the contour reflects normal wall motion the contour is classified as systole or diastole, the method further comprising:
    acquiring a next MR image sequence of the patient's heart during a next cardiac phase;
    segmenting the left ventricle of the patient's heart in the next MR image sequence, wherein the segmentation produces next endocardial and epicardial contours;
    representing at least one of the next contours in polar or radial coordinates and computing its Fourier transform, wherein the Fourier transform produces Fourier descriptors for the next contour;
    putting a vector of the Fourier descriptors for the next contour into the classifier, wherein the classifier classifies the next contour as systole or diastole;
    analyzing the contour classifications made by the classifier during the original and next cardiac phases; and
    alerting the medical practitioner that abnormal wall motion has been detected when the contour classification is the same in both the original and next cardiac phases.

10. The method of claim 1, wherein only magnitude is used as the vector of the Fourier descriptors input to the classifier.

11. A system for monitoring cardiac function of a patient during a magnetic resonance imaging (MRI) procedure, comprising:
    a memory device for storing a program:
    a processor in communication with the memory device, the processor operative with the program to:
    acquire an MR image sequence of the patient's heart during a cardiac phase;
    segment a left ventricle of the patient's heart in the MR image sequence, wherein the segmentation produces endocardial and epicardial contours;
    represent at least one of the contours in polar or radial coordinates and compute its Fourier transform, wherein the Fourier transform produces Fourier descriptors for the contour;
    put a vector of the Fourier descriptors into a classifier, wherein the classifier determines whether the contour reflects normal wall motion in the cardiac phase or whether the contour reflects abnormal wall motion in the cardiac phase by using a confidence measure; and
    alert a medical practitioner when abnormal wall motion is detected,
    wherein the confidence measure is defined by $$p(x) = \sum_C p(x \mid c_j) \cdot p(c_j) \geq \varepsilon,$$

where $c_j$ is class 1 for no contraction and class 2 for contraction, and $\varepsilon$ is the minimal unconditional probability of observation x to classify x in either of the classes, wherein contours reflective of abnormal wall motion are surrounded by contours reflective of normal wall motion in polar coordinates.

12. The system of claim 11, wherein the classifier is trained.

13. The system of claim 12, wherein the classifier is trained prior to start of the MRI procedure by observing normal wall motion during systole and diastole cardiac phases of the patient's heart and setting a baseline threshold for the normal wall motion in each of these phases.

14. The system of claim 13, wherein the training is supervised or unsupervised.

15. The system of claim 13, wherein the confidence measure is compared against the baseline threshold for the normal wall motion in the systole and diastole cardiac phases and if the confidence measure is below its respective baseline threshold the contour reflects abnormal wall motion.

16. The system of claim 11, wherein the processor is further operative with the program to:
    display real-time images of the patient's heart during the MRI procedure.

17. The system of claim 11, wherein the wall is a myocardial wall.

18. The system of claim 11, wherein the MRI procedure comprises an MRI-guided intervention or an MRI stress test.

19. A non-transitory computer readable medium tangibly embodying a program of instructions executable by a processor to perform method steps for monitoring cardiac function of a patient during a magnetic resonance imaging (MRI) procedure, the method steps comprising:
    acquiring an MR image sequence of the patient's heart during a cardiac phase;
    segmenting a left ventricle of the patient's heart in the MR image sequence, wherein the segmentation produces endocardial and epicardial contours;
    representing at least one of the contours in polar or radial coordinates and computing its Fourier transform, wherein the Fourier transform produces Fourier descriptors for the contour;
    putting a vector of the Fourier descriptors into a classifier, wherein the classifier determines whether the contour reflects normal wall motion in the cardiac phase or whether the contour reflects abnormal wall motion in the cardiac phase by using a confidence measure; and
    alerting a medical practitioner when abnormal wall motion is detected,
    wherein the confidence measure is defined by $$p(x) = \sum_C p(x \mid c_j) \cdot p(c_j) \geq \varepsilon,$$

where $c_j$ is class 1 for no contraction and class 2 for contraction, and $\varepsilon$ is the minimal unconditional probability of observation x to classify x in either of the classes, wherein contours reflective of abnormal wall motion are surrounded by contours reflective of normal wall motion in polar coordinates.

20. The computer readable medium of claim 19, wherein the classifier is trained.

21. The computer readable medium of claim 20, wherein the classifier is trained prior to start of the MRI procedure by observing normal wall motion during systole and diastole cardiac phases of the patient's heart and setting a baseline threshold for the normal wall motion in each of these phases.

22. The computer readable medium of claim 21, wherein the training is supervised or unsupervised.

23. The computer readable medium of claim 21, wherein the confidence measure is compared against the baseline threshold for the normal wall motion in the systole and diastole cardiac phases and if the confidence measure is below its respective baseline threshold the contour reflects abnormal wall motion.

24. The computer readable medium of claim 19, the method steps further comprising:
    displaying real-time images of the patient's heart during the MRI procedure.

25. The computer readable medium of claim 19, wherein the wall is a myocardial wall.

26. The computer readable medium of claim 19, wherein the MRI procedure comprises an MRI-guided intervention or an MRI stress test.

* * * * *